US010881601B2

(12) United States Patent
Rosario-Melendez et al.

(10) Patent No.: US 10,881,601 B2
(45) Date of Patent: Jan. 5, 2021

(54) COSMETIC COMPOSITIONS CAPABLE OF FORMING A MULTILAYER STRUCTURE AFTER APPLICATION TO A KERATINOUS MATERIAL

(71) Applicant: L'OREAL, Paris (FR)

(72) Inventors: Roselin Rosario-Melendez, New York, NY (US); Rita Jaky El-Khouri, Walnut Creek, CA (US)

(73) Assignee: L'OREAL, Paris (FR)

( * ) Notice: Subject to any disclaimer, the term of this patent is extended or adjusted under 35 U.S.C. 154(b) by 67 days.

(21) Appl. No.: 15/719,788

(22) Filed: Sep. 29, 2017

(65) Prior Publication Data

US 2019/0099359 A1    Apr. 4, 2019

(51) Int. Cl.

| | |
|---|---|
| *A61K 8/895* | (2006.01) |
| *A61K 8/92* | (2006.01) |
| *A61K 8/41* | (2006.01) |
| *A61K 8/89* | (2006.01) |
| *A61K 8/891* | (2006.01) |
| *A61K 8/03* | (2006.01) |
| *A61K 8/91* | (2006.01) |
| *A45D 34/04* | (2006.01) |
| *A61K 8/31* | (2006.01) |
| *A61K 8/37* | (2006.01) |
| *A61K 8/892* | (2006.01) |
| *A61K 8/893* | (2006.01) |
| *A61Q 1/06* | (2006.01) |

(52) U.S. Cl.
CPC .............. *A61K 8/891* (2013.01); *A45D 34/04* (2013.01); *A61K 8/03* (2013.01); *A61K 8/31* (2013.01); *A61K 8/375* (2013.01); *A61K 8/89* (2013.01); *A61K 8/892* (2013.01); *A61K 8/893* (2013.01); *A61K 8/91* (2013.01); *A61Q 1/06* (2013.01); *A61K 2800/30* (2013.01); *A61K 2800/87* (2013.01); *A61K 2800/882* (2013.01)

(58) Field of Classification Search
CPC ............. A61K 8/89; A61K 8/891; A61K 8/03
See application file for complete search history.

(56) References Cited

U.S. PATENT DOCUMENTS

| | | |
|---|---|---|
| 4,767,741 A | 8/1988 | Komor et al. |
| 5,882,635 A | 3/1999 | Ramin et al. |
| 5,985,297 A | 11/1999 | Mellul et al. |
| 6,019,962 A | 2/2000 | Rabe et al. |
| 6,071,503 A | 6/2000 | Drechsler et al. |
| 6,340,466 B1 | 1/2002 | Drechsler et al. |
| 6,406,683 B1 | 6/2002 | Drechsler et al. |
| 6,482,398 B1 | 11/2002 | Rabe et al. |
| 6,620,417 B1 | 9/2003 | Jose et al. |
| 6,811,770 B2 | 11/2004 | Ferrari et al. |
| 7,785,574 B2 | 8/2010 | Bobka et al. |
| 9,205,039 B2 | 12/2015 | Brown et al. |
| 2001/0031268 A1 | 10/2001 | Baldwin et al. |
| 2004/0141933 A1* | 7/2004 | Luo ........................ A61K 8/25 424/64 |
| 2005/0089498 A1 | 4/2005 | Patil et al. |
| 2005/0186166 A1 | 8/2005 | Patil et al. |
| 2005/0201961 A1 | 9/2005 | Lu et al. |
| 2005/0226832 A1 | 10/2005 | Bobka et al. |
| 2005/0244355 A1 | 11/2005 | Sabino et al. |
| 2005/0249758 A1 | 11/2005 | Di Puccio Pagano |
| 2006/0292096 A1* | 12/2006 | Yu ........................ A61K 8/891 424/64 |
| 2007/0093619 A1 | 4/2007 | Bui et al. |
| 2008/0305056 A1 | 12/2008 | Jenni et al. |
| 2008/0305068 A1 | 12/2008 | Zheng et al. |
| 2011/0147259 A1 | 6/2011 | Binder et al. |
| 2012/0308500 A1* | 12/2012 | Hart ........................ A61K 8/29 424/64 |
| 2013/0164229 A1* | 6/2013 | Mendoza ................. A61K 8/31 424/59 |
| 2014/0154196 A1 | 6/2014 | Cavazzuti et al. |
| 2014/0154199 A1 | 6/2014 | Dussaud et al. |
| 2015/0366779 A1 | 12/2015 | Bui et al. |

(Continued)

FOREIGN PATENT DOCUMENTS

| | | |
|---|---|---|
| WO | 2014095821 | 6/2014 |
| WO | 2015193413 A1 | 12/2015 |

(Continued)

OTHER PUBLICATIONS

PCT/US2017/25370, filed Mar. 31, 2017, WO 2017/173267, Rita Jaky El-Khouri.
U.S. Appl. No. 15/144,698, filed May 2, 2016, US-2017-0281518, Rita Jaky El-Khouri.
PCT/US2017/25376, filed Mar. 31, 2017, WO 2017/173270, Rita Jaky El-Khouri.
U.S. Appl. No. 15/144,622, filed May 2, 2016, US-2017-0281478, Rita Jaky El-Khouri.
U.S. Appl. No. 15/144,716, filed May 2, 2016, US-2017-0281520, Rita Jaky El-Khouri.

(Continued)

*Primary Examiner* — Kyle A Purdy
(74) *Attorney, Agent, or Firm* — Polsinelli PC

(57) ABSTRACT

Provided are high slip and shine cosmetic compositions capable of forming a multilayer structure after application to a keratinous material. Certain compositions comprise
 (a) Component A which comprises
  (i) about 0.01% to 60% by weight of least one silicone-containing and/or hydrocarbon-containing film forming agent;
  (ii) about 0.01 to 20% by weight of at least one phenylated silicone;
  (iii) about 0.01 to 20% by weight of at least one siloxane polymer wax; and
 (b) Component B which comprises;
  (i) about 0.01% to 90% by weight of the composition of one or more silicone compounds in amounts sufficient to achieve a viscosity of about 1,000 cSt to 10,000,000 cSt;
wherein the Component A and Component B are immiscible.

20 Claims, No Drawings

(56) References Cited

U.S. PATENT DOCUMENTS

| | | |
|---|---|---|
| 2015/0366782 A1 | 12/2015 | Bui et al. |
| 2017/0281478 A1 | 10/2017 | El-Khouri |
| 2017/0281518 A1 | 10/2017 | El-Khouri |
| 2017/0281519 A1 | 10/2017 | El-Khouri |
| 2017/0281520 A1 | 10/2017 | El-Khouri |
| 2017/0281521 A1 | 10/2017 | El-Khouri |

FOREIGN PATENT DOCUMENTS

| | | |
|---|---|---|
| WO | 2017173267 | 3/2017 |
| WO | 2017173270 | 3/2017 |

OTHER PUBLICATIONS

U.S. Appl. No. 15/253,071, filed Aug. 31, 2016, US-2017-0281521, Rita Jaky El-Khouri.
U.S. Appl. No. 15/253,114, filed Aug. 31, 2016, US-2017-0281519, Rita Jaky El-Khouri.
U.S. Appl. No. 15/857,045, filed Dec. 28, 2017, Rita Jaky El-Khouri.
U.S. Appl. No. 15/445,634, filed Feb. 28, 2017, Rita Jaky El-Khouri.
U.S. Appl. No. 15/445,684, filed Feb. 28, 2017, Rita Jaky El-Khouri.
U.S. Appl. No. 15/720,341, filed Sep. 29, 2017, Rita Jaky El-Khouri.
U.S. Appl. No. 15/857,066, filed Dec. 28, 2017, Rita Jaky El-Khouri.
"Xiameter® PMX-200 Silicone Fluid 30,000 CS," Xiameter® Material Safety Data Sheet, Version 3.0, published Sep. 13, 2017, p. 1-12.
"Xiameter® PMX-200 Silicone Fluid, 5,000-60,000 est," Xiameter® from Dow Corning, published Feb. 18, 2015, p. 1-3.
"Mega Last Liquid Lipstick Liquid Lipstick: Improved Color Intensity, Non-transfer," Formulation 01451, Dow Corning, Formulation Information Color Cosmetics©, 2010 Dow Corning Corporation, p. 1-2.
Alex C.M. Kuo, "Poly(dimethylsiloxane)," Polymer Data Handbook©, 1999 by Oxford University Press, Inc., p. 1-25.
International Search Report and Written Opinion dated Jul. 11, 2017 in PCT/US 2017/025376.
"Triethoxy Caprylylsilane Treatment-11S," Kobo Products Inc., published Jul. 14, 2017.
"Introduction to Silicone Fluids," Clearco Products Co., Inc.,p. 1-4.

\* cited by examiner

COSMETIC COMPOSITIONS CAPABLE OF FORMING A MULTILAYER STRUCTURE AFTER APPLICATION TO A KERATINOUS MATERIAL

FIELD OF THE INVENTION

The present invention relates to cosmetic compositions capable of forming a multilayer structure after application to a keratinous material. Such compositions allow for benefits associated with multilayer cosmetic products without having to engage in a multi-step application process.

DISCUSSION OF THE BACKGROUND

Many cosmetic compositions, including pigmented cosmetics such as lipsticks, foundations and eye shadows, have been formulated in an attempt to possess long wearing properties upon application. Unfortunately, many of these compositions do not generally possess both good long-wear/transfer-resistance properties as well as good application properties, good comfort properties and/or good appearance properties (for example, shine, or matte properties).

For example, with respect to lip products, commercial products containing silicon resins such as MQ resins are known. Such products are known to provide good long wear properties and/or transfer-resistance. However, such products possess poor application properties, poor feel upon application (for example, feel rough) and poor shine or gloss properties owing to the film formed by the MQ resin (for example, a matte appearance). Therefore, a second composition (topcoat) is separately applied to such products to improve poor properties of the compositions to make the products acceptable to consumers. Furthermore, the topcoat composition must be reapplied continually so that the product remains acceptable to consumers, meaning that the products are effectively not "long-wearing" as they require constant maintenance and reapplication.

Also, with respect to foundations, such products can provide good long wear properties and/or transfer-resistance. However, such long-wearing/transfer-resistant products can possess poor application and/or feel upon properties application, as well as poor matte properties.

Thus, there remains a need for improved "single step" cosmetic compositions having improved cosmetic properties, particularly good wear, feel, shine, gloss and/or matte characteristics upon application, while also being a stable formulation.

SUMMARY OF THE INVENTION

The present invention relates to cosmetic compositions capable of forming a multilayer structure after application to a keratinous material. In one or more embodiments, the composition comprises:
(a) Component A which comprises
  (i) about 0.01% to 60% by weight with respect to the total weight of the composition of at least one silicone-containing and/or hydrocarbon-containing film forming agent having at least one glass transition temperature which is lower than normal human body temperature;
  (ii) about 0.01 to 20% by weight with respect to the total weight of the composition of at least one phenylated silicone;
  (iii) about 0.01 to 20% by weight with respect to the total weight of the composition of at least one siloxane polymer wax; and
(b) Component B which comprises;
  (i) about 0.01% to 90% by weight with respect to the total weight of the composition of one or more silicone compounds in amounts sufficient to achieve a viscosity of about 1,000 cSt to 10,000,000 cSt;
wherein the Component A and Component B are immiscible, wherein the weight ratio of silicone-containing and/or hydrocarbon-containing film forming agent(s) in Component A to silicone compound(s) in Component B is from about 1:50 to 50:1.

In one or more embodiments, the cosmetic composition comprises at least two immiscible components prior to application. In some embodiments, the cosmetic composition is anhydrous. In one or more embodiments, the at least one phenylated silicone is selected from the group consisting of trimethylsiloxyphenyl dimethicone, diphenylsiloxy phenyl trimethicone; trimethyl pentaphenyl trisiloxane; trimethyl pentaphenyl trisiloxane, and combinations thereof. In some embodiments, the at least one siloxane polymer wax is selected from the group consisting of bis-stearyl dimethicone, stearyl dimethicone, bis stearoxy dimethicone, and combinations thereof.

In one or more embodiments, the composition further comprises (iv) about 0.01 to 10% by weight with respect to the total weight of the composition of at least one triester of glycerin and a fatty acid. In some embodiments, the at least one triester of glycerin and a fatty acid comprises trihydroxystearin. In one or more embodiments, the at least one silicone-containing and/or hydrocarbon-containing film forming agent is present in an amount of about 15% to 60% by weight with respect to the total weight of the composition. In some embodiments, the one or more silicone compounds are present in amount of about 0.01% to about 80% by weight with respect to the total weight of the composition and in amounts sufficient to achieve a viscosity of 30,000 cSt to 70,000 cSt. In one or more embodiments, the weight ratio of film forming agent(s) in Component A to silicone compound(s) in Component B is from 50:1 to 1:2. In some embodiments, the silicone compound comprises at least one polymer selected from the group consisting of a silicone gum, a silicone fluid, and mixtures thereof.

In one or more embodiments, Component A comprises at least one silicone-containing film forming agent selected from the group consisting of a silicone resin, a silicone acrylate copolymer, and mixtures thereof. In some embodiments, the at least one silicone-containing film forming agent comprises a silsesquioxane. In one or more embodiments, Component A comprises at least one hydrocarbon-containing film forming agent selected from the group consisting of polysaccharides, high viscosity esters, polybutenes, polyisobutenes, polyhydrogenated butenes, acrylic polymers, acrylate copolymers, vinyl pyrrolidone (VP) containing homopolymers and copolymers, polyurethanes, polyolefins and mixtures thereof. In some embodiments, cosmetic composition does not comprise a fluorinated compound.

Any of the above embodiments may be combined with the others. For example, in some embodiments the composition comprises:
(a) Component A which comprises
  (i) about 20% to 40% by weight with respect to the total weight of the composition of polypropylsilsesquioxane, acrylates/dimethicone copolymer and combinations thereof;

(ii) about 5 to 15% by weight with respect to the total weight of the composition of at least one phenylated silicone;

(iii) about 1 to 10% by weight with respect to the total weight of the composition of at least one siloxane polymer wax;

(iv) about 0.1 to 2% by weight with respect to the total weight of the composition of at least one triester of glycerin and a fatty acid; and (b) Component B which comprises;

(i) about 10% to 30% by weight with respect to the total weight of the composition of one or more silicone compounds selected from the group consisting of dimethicone, dimethiconol and combinations thereof in amounts sufficient to achieve a viscosity of about 1,000 cSt to 100,000 cSt;

wherein the Component A and Component B are immiscible, and wherein the weight ratio of silicone-containing and/or hydrocarbon-containing film forming agent(s) in Component A to silicone compound(s) in Component B is from about 50:1 to 1:2.

Another aspect of the invention pertains to a kit. In one or more embodiments, the kit comprises (a) any of the compositions described herein; (b) at least one container which contains the cosmetic composition according to claim 1; and (c) at least one applicator. In one or more embodiments, the at least one container is configured to mix the cosmetic composition.

Another aspect of the invention pertains to methods of applying the cosmetic compositions described herein. In one or more embodiments, mixing the cosmetic composition to form a mixed composition in which Component A and Component B are temporarily miscible, and applying the mixed composition to the keratinous material.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied.

"Polymer" as used herein means a compound which is made up of at least two monomers.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2, 3, 4, 5, 6, 7, 8, 9, 10, 11, 12, 13, 14 or 15 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Adhesion" as used herein refers to the quality exhibited by compositions that adhere to a substrate after application. Adhesion may be evaluated by any method known in the art for evaluating such. For example, samples to be tested for adhesion properties can be deposited onto a surface such as a bioskin substrate or Byko-Charts Black Scrub Panels P122-10N (6.50×17.00 inches). After drying, a piece of ASTM cross hatch tape (Permacel 99/PA-28060/51596) can be placed on the sample, and removed at a 180° angle. Then, it can be determined how much of the sample is adhered to the tape. For example, a rating scale such as a scale of 1-3 can be used to assess the degree of sample removal from the substrate onto the tape, in which 1 is essentially no removal, 2 is some removal, and 3 is essentially complete removal.

The term rub-off resistance as used herein refers to physical abrasion such as rubbing the human skin with the hands or clothes or other physical interaction. It can also be described as the ability to hold active ingredients on the skin or prevent the removal of active ingredients from the skin or a substrate such as Byko-Charts Black Scrub Panels P122-10N (6.50×17.00 inches) or bioskin by abrasion or other physical interaction.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to the skin and evaluating the color of the composition after an extended period of time. For example, the color of a composition may be evaluated immediately following application to skin and these characteristics may then be re-evaluated and compared after a certain amount of time. Further, these characteristics may be evaluated with respect to other compositions, such as commercially available compositions. Alternatively or additionally, long wear properties may be evaluated by applying a sample, allowing it to dry, and then abrading the sample to determine removal/loss of sample.

The cosmetic compositions and methods of the present invention can comprise, consist of, or consist essentially of the essential elements and limitations of the invention described herein, as well as any additional or optional ingredients, components, or limitations described herein or otherwise useful in personal care.

Compositions Capable of Forming a Multilayer Structure

In accordance with various embodiments of the present invention, cosmetic compositions capable of forming a multilayer structure after application to a keratinous material are provided. Such compositions allow for benefits associated with multilayer cosmetic products without having to engage in a multi-step application process. In one or more embodiments, such compositions are suitable as lipsticks, lip glosses, foundations, eye shadows and other skin compositions.

In accordance with one or more embodiments of the present invention, the cosmetic compositions of the present invention comprise at least two Components, hereinafter referred to as "Component A" and "Component B." In one or more embodiments, both Component A and Component B comprise silicone. Component A, for example, may comprise a silicone-containing film-forming agent. Component B, for example, may comprise a silicone gum. In some embodiments, Component A comprises a hydrocarbon film forming agent, and Component B comprises a silicone compound. Again, Component B, for example, may comprise a silicone gum. In one or more embodiments, Component A may comprise both a silicone-containing film forming agent as well as a hydrocarbon-containing film forming agent.

Component A is the component of the compositions of the present invention which forms the layer of the multilayer structure which is closest to the keratinous material after application of the composition to the keratinous material. This layer of the multilayer structure is hereinafter referred to as "Layer A." In accordance with preferred embodiments, Component A/Layer A has an affinity for the surface of the keratinous material owing to the surface energy characteristics between the two.

Component B is the component of the compositions of the present invention which forms the layer of the multilayer structure which is farthest away from the keratinous material after application of the composition to the keratinous material. This layer of the multilayer structure is hereinafter referred to as "Layer B." In accordance with preferred embodiments, Component B/Layer B has an affinity for the air interface.

In accordance with the present invention, all weight amounts and ratios set forth herein referring to Component A and Component B refer to amounts of active material (that is, non-volatile material) in these components. Similarly, all weight amounts and ratios set forth herein referring to Layer A and Layer B refer to amounts of active material as Layer A and Layer B are present after evaporation of volatile solvent.

Prior to application to a keratinous material, Component A and Component B are immiscible in the compositions of the present invention. Preferably, immiscibility of the immiscible components results from an incompatibility between the two components when the composition is at rest, incompatibility between the two components after application to a keratinous material, or both.

In one or more embodiments, immiscibility of the immiscible components results from differences such as, for example, differences in viscosity, glass transition temperature, interfacial tension, solubility parameters, density, and/or chemical/structural incompatibility of the components, and/or differences induced by temperature and/or pressure.

For example, immiscibility of the immiscible components when the composition is at rest can result from, for example, chemical/structural incompatibility, differences in the interfacial tension between the components such as, for example, differences in the interfacial tension between the phases within mutually compatible solvent(s), differences in viscosity, differences in the glass transition temperatures of the polymers within each phase and/or differences induced by temperature and/or pressure.

For example, immiscibility of the immiscible components when the composition is being applied can result from, for example, chemical/structural incompatibility, differences in the interfacial tension between the components, differences in density of the components after solvent evaporation, and/or differences induced by temperature and/or pressure.

In one or more embodiments, immediately prior to application and/or during application to a keratinous material, the composition of the present invention is mixed or blended such that Component A and Component B are temporarily miscible upon application of the composition of the present invention to a keratinous material.

After the composition of the present invention has been applied to a keratinous material, Component A separates from Component B. As the composition dries on the keratinous material to which it has been applied, immiscible Component A and Component B form a multilayer structure comprising Layer A and Layer B, respectively, on the keratinous material such as, for example:

| LAYER B |
| LAYER A |
| KERATINOUS MATERIAL |

According to one or more embodiments of the present invention, after compositions of the present invention have been applied to a keratinous material, Component B results in Layer B which is level: that is, Layer B is planar such that it may have refractive properties to impart shine to the composition. In accordance with these embodiments, Component B has self-leveling properties: it results in a level Layer B after application. The shine of such compositions can be enhanced, if desired, by addition of one or more shine or gloss enhancing agents having high refractive index properties. Alternatively, such compositions can be provided with matte properties by addition of one or more mattifying agents.

According to preferred embodiments of the present invention, after compositions of the present invention have been applied to a keratinous material, Component B results in Layer B which is not-level: that is, Layer B is not planar such that it imparts matte properties to the composition. In accordance with these embodiments, Component B does not have self-leveling properties: it results in a non-level Layer B after application. The matte properties of such compositions can be enhanced, if desired, by addition of one or more mattifying agents. Alternatively, such compositions can be provided with shine/luminosity properties by addition of one or more shine or gloss enhancing agents having high refractive index properties. Another benefit of the compositions is when used as a base layer/primer, the self-leveling nature of the compositions may provide a smoothing surface, thereby reducing imperfections in the skin.

In accordance with the present invention, the multilayer structure comprises Layer A and Layer B. In certain instances, depending on factors such as ingredient ratios, ingredient concentrations, solvent evaporation characteristics, and Tg of polymers, the layers might be intermixed slightly with each other after application to a keratinous material, resulting in Layer A having a larger amount of A and a smaller amount of B greater and/or Layer B having a larger amount of B and a smaller amount of A. Preferably, Layer A comprises 40% or less of Layer B, preferably 30% or less of Layer B, preferably 20% or less of Layer B, preferably 10% or less of Layer B, and preferably 5% or less of Layer B, including all ranges and subranges therebetween. Similarly, preferably, Layer B comprises 40% or less of Layer A, preferably 30% or less of Layer A, preferably 20% or less of Layer A, preferably 10% or less of Layer B, and preferably 5% or less of Layer A, including all ranges and subranges therebetween.

Factors affecting the separation of Component A and Component B after application to a keratinous material can include, for example, those properties discussed above including but not limited to the surface energy of the substrate, the density of each Component, the evaporation properties of the solvent(s), the Tg of the film formers, and/or the viscosity of the film formers.

Although not wishing to be bound by any particular theory, it is believed that Component A has a surface energy properties closer to the surface energy properties of the keratinous material to which it is applied than Component B. For example, the surface energy of skin is estimated to be 36 mN/m. Accordingly, where Component A has a surface energy of about 36 mN/m, it is believed that Component A can migrate to the skin. Component B would preferably have a lower surface energy, making it more likely that it would migrate toward the air interface.

Although not wishing to be bound by any particular theory, it is believed that interfacial tension of Components A and B affects phase separation (in particular, the rate at which the Components A and B separate after application). It is believed that such phase separation can be affected by differences such as those discussed above such as, for example, differences in temperature of the Components A and B, in the Tg of the Components A and B (the higher the Tg of a component, the longer it will take for phase separation), in the weight fraction of the film formers, and/or in the pressure of the Components A and B.

Such differences will also be discussed further below.

Glass Transition Temperature (Tg)

According to preferred embodiments, Component A and/or Component B comprises at least one silicone- and/or hydrocarbon-containing film forming agent having at least one glass transition temperature lower than 60° C., preferably lower than 55° C., preferably lower than 50° C., and preferably lower than normal human body temperature (98.6° F. or 37° C.). Preferably, Component A and/or Component B comprises at least one silicone- and/or hydrocarbon-containing film forming agent which has all of its glass transition temperature(s) below human body temperature (98.6° F. or 37° C.). A plasticizer can be added to adjust Tg of the film forming agent(s) as is known in the art. According to preferred embodiments, Layer A and Layer B both comprise at least one forming agent having a glass transition temperature of less than 37° C.

A preferred method of determining Tg is to remove all volatile solvent from the Layer, and determining Tg by Differential Scanning calorimetry.

Density

According to preferred embodiments, Component A and Component B have different density properties, and the difference is such that Component A and Component B are immiscible in the compositions of the present invention. Preferably, Component A/Layer A and Component B/Layer B have a density difference of 0.001-1 kg/m3, preferably 0.005-0.8 kg/m3, and preferably 0.01-0.6 kg/m3.

Temperature

According to preferred embodiments, Component A and Component B are affected by temperature, and the effect is such that Component A and Component B are immiscible in the compositions of the present invention at temperatures below 50° C. for a predetermined amount of time as is known in the art unlike emulsions which are considered to be stable under such conditions.

Weight Fraction

According to preferred embodiments, Component A and/or Component B comprises at least one polymer such as, for example a film forming agent having a critical molecular weight of entanglement (Mc) such that:

If present in Component A, the at least one polymer has an $Mc < wMw$, where w=weight fraction and Mw=molecular weight of the polymer; and If present in Component B, the at least one polymer has $Mc \leq wMw \leq 10^8$ g/mol.

Further, according to preferred embodiments, the viscosity of the at least one polymer in Component B is greater than 350 cSt, preferably greater than 500 cSt, preferably greater than 750 cSt, and preferably greater than 1000 cSt, including all ranges and subranges therebetween.

Ingredients

Component A and Component B can differ in various ways based primarily on the different functionalities associated with Layer A and Layer B. For example, where Layer A performs a transfer-resistance or adherence function, ingredients of Component A can be chosen to effect transfer-resistance or adherence. Similarly, where Layer A performs a color-enhancing function, at least one coloring agent can be added to Component A. And, for example, where Layer B performs a or shine-enhancing function and/or and provides a better feel (for example, affords a more comfortable feeling) and/or provides a barrier layer to inhibit color transfer, ingredients of Component B can be chosen to effect gloss, shine, comfort and/or barrier layer properties. However, it should be understood that at the interface of Layer A and Layer B, the interface of Layer A may possess properties more associated with Layer B (for example, shine) while Layer B may possess properties more associated with Layer A (for example, adhesion).

According to preferred embodiments, Component A comprises at least one silicone- and/or hydrocarbon-containing film forming agent, at least one coloring agent, or both, and Layer A provides adhesion, transfer-resistance and/or color properties to the multilayer structure. According to such embodiments, Component B may comprise at least one shine-enhancing agent, at least one comfort agent and/or at least one barrier agent, and Layer B provides shine, comfort and/or a barrier properties to the multilayer structure.

In some embodiments, the compositions comprise less than about 1% or 0.5% fluorinated compound, or do not contain a fluorinated compound.

According to preferred embodiments, the compositions of the present invention contain less than 0.5% fluorinated compound. According to preferred embodiments, the compositions of the present invention contain no fluorinated compound.

According to preferred embodiments, at least one of the same solvent(s) is used in Component A and Component B. Preferably, of total solvent present in each Component, the majority in each Component is the same.

According to preferred embodiments, the weight ratio of Component A to Component B is from 1:50 to 1.5:1, 1:75 to 1.5:1, from 1:50 to 1.5:1, or from 1:20 to 1.5:1, including all ranges and subranges therebetween.

Examples of acceptable ingredients added to Component A and/or Component B are discussed below.

Film Forming Agent (Film Former)

Compositions of the present invention may comprise at least one silicone- and/or hydrocarbon-containing film forming agent. Silicone and hydrocarbon-containing film forming agents are known in the art, and any silicone- and/or hydrocarbon-containing film forming agent may be used. According to preferred embodiments, at least one silicone and/or hydrocarbon-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one silicone and/or hydrocarbon-containing film forming agent has all of its glass transition temperature(s) below 60° C., preferably below than 55° C., preferably below than 50° C., and preferably below than normal human body temperature (98.6° F.). The Tg property of the at least one silicone and/or hydrocarbon-containing film forming agent can result from various ways known in the art such as, for example, the Tg of the silicone and/or hydrocarbon-containing film forming agent itself, the combination of different film forming agents to achieve a Tg lower than normal human body temperature, or the combination of film forming agent(s) and plasticizer(s) to achieve a Tg lower than normal human body temperature.

According to preferred embodiments, the film forming agent(s) is/are preferably present in an amount of from about 0.05, 0.1, 0.5, 1, 2, 3, 4, 5, 10, 15, 20 or 25% to about 25, 30, 35, 45, 50, 55, 60, 65, 70, 80 or 90% by weight.

Hydrocarbon-Containing Film Forming Agents (Film Former)

Compositions of the present invention may comprise at least one hydrocarbon-containing film forming agent. As used herein, "hydrocarbon-containing film forming agent" refers to a film forming agent comprising at least about 2.5, 5, 10, 20, 30, 40, 50, 60, 70, 80, 90, 95, or 99% hydrocarbon by weight. In further embodiments, the hydrocarbon-containing film forming agent comprises less than about 5 or 1% silicone resins, and in yet further embodiments, no silicone resins.

Hydrocarbon-containing film forming agents are known in the art, and any hydrocarbon-containing film forming agent may be used. According to preferred embodiments, at least one hydrocarbon-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one hydrocarbon-containing film forming agent has all of its glass transition temperature(s) below 60° C., preferably below than 55° C., preferably below than 50° C., and preferably below than normal human body temperature (98.6° F.). The Tg property of the at least one hydrocarbon-containing film forming agent can result from various ways known in the art such as, for example, the Tg of the hydrocarbon-containing film forming agent itself, the combination of different film forming agents to achieve a Tg lower than normal human body temperature, or the combination of film forming agent(s) and plasticizer(s) to achieve a Tg lower than normal human body temperature.

Examples of acceptable classes of film forming agents include acrylic polymers, acrylate copolymers, vinyl pyrrolidone (VP) containing homopolymers and copolymers, polyurethanes, polyolefins and mixtures thereof.

Acrylic Polymers

Acceptable acrylic polymer film forming agents are known in the art and include, but are not limited to, those disclosed in U.S. patent application 2004/0170586 and U.S. patent application 2011/0020263, the entire contents of which are hereby incorporated by reference in their entirety.

"Acrylic polymer film formers" as used herein refers to polymers that are film forming agents and which are based upon one or more (meth)acrylic acid (and corresponding (meth)acrylate) monomers or similar monomers. In further embodiments, the acrylic polymer film formers do not contain a silicone or siloxane group.

Non-limiting representative examples of such film forming agents include copolymers containing at least one apolar monomer, at least one olefinically unsaturated monomer, and at least one vinylically functionalized monomer.

For the apolar monomers, acrylic monomers which comprise acrylic and methacrylic esters with alkyl groups composed of 4 to 14 C atoms, preferably 4 to 9 C atoms are preferred. Examples of monomers of this kind are n-butyl acrylate, n-butyl methacrylate, n-pentyl acrylate, n-pentyl methacrylate, n-amyl acrylate, n-hexyl acrylate, hexyl methacrylate, n-heptyl acrylate, n-octyl acrylate, n-octyl methacrylate, n-nonyl acrylate, isobutyl acrylate, isooctyl acrylate, isooctyl methacrylate, and their branched isomers, such as, for example, 2-ethylhexyl acrylate, 2-ethylhexyl methacrylate.

For olefinically unsaturated monomers, it is preferred to use monomers having functional groups selected from hydroxyl, carboxyl, sulphonic acid groups, phosphonic acid groups, acid anhydrides, epoxides, and amines. Particularly preferred examples of olefinically unsaturated monomers include acrylic acid, methacrylic acid, itaconic acid, maleic acid, fumaric acid, crotonic acid, aconitic acid, dimethylacrylic acid, beta-acryloyloxypropionic acid, trichloracrylic acid, vinylacetic acid, vinylphosphonic acid, itaconic acid, maleic anhydride, hydroxyethyl acrylate, hydroxypropyl acrylate, hydroxyethyl methacrylate, hydroxypropyl methacrylate, 6-hydroxyhexyl methacrylate, allyl alcohol, glycidyl acrylate, glycidyl methacrylate.

For vinylically functionalized compounds, preferred monomers include monomers which are copolymerizable with one or both of the previously discussed monomers and include, for example, methyl acrylate, ethyl acrylate, propyl acrylate, methyl methacrylate, ethyl methacrylate, benzyl acrylate, benzyl methacrylate, sec-butyl acrylate, tert-butyl acrylate, phenyl acrylate, phenyl methacrylate, isobornyl acrylate, isobornyl methacrylate, tert-butylphenyl acrylate, tert-butyl phenyl methacrylate, dodecyl methacrylate, isodecyl acrylate, lauryl acrylate, n-undecyl acrylate, stearyl acrylate, tridecyl acrylate, behenyl acrylate, cyclohexyl methacrylate, cyclopentyl methacrylate, phenoxyethyl acrylate, phenoxyethyl methacrylate, 2-butoxyethyl methacrylate, 2-butoxyethyl acrylate, 3,3,5-trimethylcyclohexyl acrylate, 3,5-dimethyladamantyl acrylate, 4-cumylphenyl methacrylate, cyanoethyl acrylate, cyanoethyl methacrylate, 4-biphenyl acrylate, 4-biphenyl methacrylate, 2-naphthyl acrylate, 2-naphthyl methacrylate, tetrahydrofurfuryl acrylate, diethylaminoethyl acrylate, diethylaminoethyl methacrylate, dimethylaminoethyl acrylate, dimethylaminoethyl methacrylate, 2-butoxyethyl acrylate, 2-butoxyethyl methacrylate, methyl 3-methoxyacrylate, 3-methoxybutyl acrylate, phenoxyethyl acrylate, phenoxyethyl methacrylate, 2-phenoxyethyl methacrylate, butyldiglycol methacrylate, ethylene glycol acrylate, ethylene glycol monomethylacrylate, methoxy-polyethylene glycol methacrylate 350, methoxy-polyethylene glycol methacrylate 500, propylene glycol monomethacrylate, butoxydiethylene glycol methacrylate, ethoxytriethylene glycol methacrylate, dimethylaminopropylacrylamide, dimethylaminopropylmethacrylamide, N-(1-methylundecyl)acrylamide, N-(n-butoxymethyl)acrylamide, N-(butoxymethyl)methacrylamide, N-(ethoxymethyl)acrylamide, N-(n-octadecyl)acrylamide, and also N,N-dialkyl-substituted amides, such as, for example, N,N-dimethylacrylamide, N,N-dimethylmethacrylamide, N-benzylacrylamides, N-isopropylacrylamide, N-tert-butylacrylamide, N-tert-octylacrylamide, N-methylolacrylamide, N-methylolmethacrylamide, acrylonitrile, methacrylonitrile, vinyl ethers, such as vinyl methyl ether, ethyl vinyl ether, vinyl isobutyl ether, vinyl esters, such as vinyl acetate, vinyl chloride, vinyl halides, vinylidene chloride, vinylidene halide, vinylpyridine, 4-vinylpyridine, N-vinylphthalimide, N-vinyllactam, N-vinylpyrrolidone, styrene, a- and p-methylstyrene, a-butylstyrene, 4-n-butylstyrene, 4-n-decylstyrene, 3,4-dimethoxystyrene, macromonomers such as 2-polystyrene-ethyl methacrylate (molecular weight Mw of 4000 to 13 000 g/mol), poly(methyl methacrylate)ethyl methacrylate (Mw of 2000 to 8000 g/mol).

An example of an acrylic polymer is a copolymer of acrylic acid, isobutyl acrylate and isobornyl acetate such as that sold under the names Pseudoblock (Chimex) and Synamer-3. In both of these commercial products, the copolymer is present with a solvent in a 1:1 ratio (50% solid). Another preferred film former is Poly(isobornyl methacrylate-8 co-isobornyl acrylate-co-isobutyl acrylate-co-acrylic acid) at 50% of active material in 50% of octyldodecyl neopentanoate, (Mexomere PAZ from Chimex).

Vinylpyrrolidone Polymers

Acceptable vinylpyrrolidone homopolymers or copolymers include, for example, crosslinked or non-crosslinked vinylpyrrolidone homopolymers such as the Polymer ACP-10, as well as copolymers produced from alpha-olefin and vinylpyrrolidone in which, preferably, the copolymer contains vinylpyrrolidone and an alkyl component containing at least one C4-C30 moiety in a concentration preferably from 10 to 80 percent such as those available from Ashland under the Ganex name such as, for example, VP/eicosene (GANEX V-220) and VP/tricontanyl copolymer (GANEX WP660).

High Viscosity Ester

In one or more embodiments, cosmetic composition of the present invention may also contains at least one high viscosity ester. Examples thereof include, but not limited to, C1-C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are C18 mono- and/or di-unsaturated and behenic, in a molar ratio of unsaturates:behenic of 1:7 to 3:5. In another embodiment, the sugar polyester is the octaester of sucrose in which there are about 7 behenic fatty acid moieties and about oleic acid moiety in the molecule. Other materials may include cottonseed oil or soybean oil fatty acid esters of sucrose.

In one or more embodiments, the high viscosity ester comprises sucrose acetate isobutyrate. One example of a suitable sucrose acetate isobutyrate compound is SAIB-100®, commercially available from Eastman®, Kingsport, Tenn. This ester has a viscosity of about 100,000 cps at 30° C. and a refractive index of about 1.5 at 20° C.

Acrylic Polymers

Acceptable acrylic polymer film forming agents are known in the art and include, but are not limited to, those disclosed in U.S. patent application 2004/0170586 and U.S. patent application 2011/0020263, the entire contents of which are hereby incorporated by reference in their entirety.

Silicone-Containing Film Forming Agent (Film Former)

Compositions of the present invention may comprise at least one silicone-containing film forming agent. As used herein, "silicone-containing film forming agent" refers to a film forming agent that contains silicone. In one or more embodiments, "silicone-containing film forming agent" includes polymers that contain at least about 2.5%, 5%, 10%, 20%, 30%, 40%, 50%, 60%, 70%, 80%, 90%, 95%, or 99% silicone by weight. Silicone-containing film forming agents are known in the art, and any silicone-containing film forming agent may be used. According to preferred embodiments, at least one silicone-containing film forming agent having at least one glass transition temperature lower than 60° C., preferably lower than 55° C., preferably lower than 50° C., and preferably lower than normal human body temperature (98.6° F.), is included in the composition of the present invention. Preferably, the at least one silicone-containing film forming agent has all of its glass transition temperature(s) below 60° C., preferably below than 55° C., preferably below than 50° C., and preferably below than normal human body temperature (98.6° F.). The Tg property of the at least one silicone-containing film forming agent can result from various ways known in the art such as, for example, the Tg of the silicone-containing film forming agent itself, the combination of different film forming agents to achieve a Tg lower than normal human body temperature, or the combination of film forming agent(s) and plasticizer(s) to achieve a Tg lower than normal human body temperature.

Examples of acceptable classes of silicone-containing film forming agents include silicone resins, silicone acrylate copolymers. vinyl pyrrolidone (VP) containing copolymers, polyurethanes, polyolefins and mixtures thereof.

In one or more embodiments, the silicone-containing film forming agent(s) is/are selected from the group consisting of silicone resins, silicone acrylate copolymers mixtures thereof.

Silicone Resin

As used herein, the term "resin" means a crosslinked or non-crosslinked three-dimensional structure. According to one or more embodiments of the present invention, Component A comprises at least one silicone acrylate. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit (CH3)3SiO1/2. This unit is considered to be monofunctional because the silicone atom only shares on oxygen when the unit is part of a polymer. The "M" unit can be represented by the following structure:

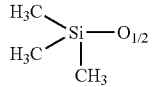

At least one of the methyl groups of the M unit may be replaced by another group, e.g., to give a unit with formula [R(CH3)2]SiO1/2, as represented in the following structure:

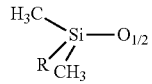

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit (CH3)2SiO2/2 wherein two oxygen atoms bonded to the silicone atom are used for binding to the rest of the polymer. The "D" unit, which is the major building block of dimethicone oils, can be represented as:

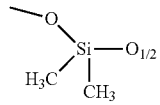

At least one of the methyl groups of the D unit may be replaced by another group, e.g., to give a unit with formula [R(CH3)2]SiO1/2.

The symbol T denotes the trifunctional unit, (CH3)SiO3/2 and can be represented as:

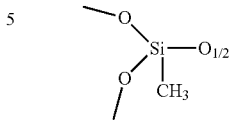

At least one of the methyl groups of the T unit may be replaced by another group, e.g., to give a unit with formula [R(CH3)2]SiO1/2.

Finally, the letter Q means a tetrafunctional unit SiO4/2 in which the silicon atom is bonded to four hydrogen atoms, which are themselves bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include siloxysilicates and silsesquioxanes.

A non-limiting example of a siloxysilicate is trimethylsiloxysilicate, which may be represented by the following formula:

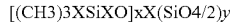

[(CH3)3XSiXO]xX(SiO4/2)y (i.e, MQ units) wherein x and y may, for example, range from 50 to 80. Silsesquioxanes, on the other hand, may be represented by the following formula:

(CH3SiO3/2)x (i.e., T Units) wherein x may, for example, have a value of up to several thousand.

Resin MQ, which is available from Wacker, General Electric and Dow Corning, is an example of an acceptable commercially-available siloxysilicate. For example, trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Suitable silicon resins comprising at least one T unit in accordance with the present invention are disclosed, for example, in U.S. patent application publication numbers 2007/0166271, 2011/0038820, 2011/0002869, and 2009/0214458, the entire contents of which are hereby incorporated by reference in their entirety.

Where the silicone resin contains at least one T unit, it may thus be, for example, a T, MT, MTQ or MDTQ resin.

According to preferred embodiments, the unit composition of the silicone resin can be at least 50% T units, or at least 70% T units, or at least 80% T units, or at least 90% T units.

In the M, D and T units listed as examples above, at least one of the methyl groups may be substituted. According to preferred embodiments, the at least one silicone resin comprising at least one trifunctional unit of formula (R)SiO3/2 is chosen from the silsesquioxanes of formula: ((R')SiO3/2)x, in which x ranges from 100 to 500 and R' is chosen, independently by trifunctional unit, from a hydrocarbon-based group containing from 1 to 10 carbon atoms or a hydroxyl group, on the condition that at least one R' is a hydrocarbon-based group. According to preferred embodiments, the hydrocarbon-based group containing from 1 to 10 carbon atoms is a methyl group. According to preferred embodiments, the at least one silicone resin comprising at least one trifunctional unit of formula (R)SiO3/2 is chosen from the silsesquioxanes of the formula: ((R')SiO3/2) x, in which x ranges from 100 to 500 and R' is chosen, independently by unit, from CH3, a hydrocarbon-based group containing from 2 to 10 carbon atoms, or a hydroxyl group, on the condition that at least one R' is a hydrocarbon-based group.

According to preferred embodiments, the T resins may contain M, D and Q units such that at least 80 mol % or at least 90 mol %, relative to the total amount of silicones, are T units. The T resins may also contain hydroxyl and/or alkoxy groups. The T resins may have a total weight of hydroxyl functions ranging from 2% to 10% and a total weight of alkoxy functions that may be up to 20%; in some embodiments, the total weight of hydroxyl functions ranges from 4% to 8% and the total weight of alkoxy functions may be up to 10%.

The silicone resin may be chosen from silsesquioxanes that are represented by the following formula: ((CH3)SiO3/2)x, in which x may be up to several thousand and the CH3 group may be replaced with an R group, as described previously in the definition of the T units. The number x of T units of the silsesquioxane may be less than or equal to 500, or it may range from 50 to 500, including all ranges and subranges therebetween. The molecular weight of the silicone resin may range from about 500, 1000, 5,000, 10,000, 15,000 or 20,000 g/molto about 30,000, 35,000, 40,000, 45,000, 50,000, 75,000 or 100,000 g/mol, including all ranges and subranges therebetween.

As suitable examples of these silicone resins containing at least one T unit, mention may be made of:
  polysilsesquioxanes of formula ((R)SiO3/2)x (T units) in which x is greater than 100, in which the R groups may independently be methyl or other substituents as defined above;
  polymethylsilsesquioxanes, which are polysilsesquioxanes in which R is a methyl group. Such polymethylsilsesquioxanes are described, for example, in U.S. Pat. No. 5,246,694, the entire contents of which is hereby incorporated by reference in its entirety;
  polypropylsilsesquioxanes, in which R is a propyl group. These compounds and their synthesis are described, for example, in patent application WO 2005/075567, the entire contents of which is hereby incorporated by reference in its entirety; and
  polyphenylsilsesquioxanes, in which R is a phenyl group. These compounds and their synthesis are described, for example, in patent application US 2004/0180011, the entire contents of which is hereby incorporated by reference in its entirety.

Examples of commercially available polymethylsilsesquioxane resins that may be mentioned include those sold: by the company Wacker under the reference Resin MK such as Belsil PMS MK: polymer comprising CH3SiO3/2 repeating units (T units), which may also comprise up to 1% by weight of (CH3)2SiO2/2 units (D units) and having an average molecular weight of about 10 000 g/mol. It is thought that the polymer is in a "cage" and "ladder" configuration as represented in the figures below. The average molecular weight of the units in "cage" configuration has been calculated as 536 g/mol. The majority of the polymer is in the "ladder" configuration with ethoxy groups at the ends. These ethoxy groups represent 4.5% by mass of the polymer. As these end groups can react with water, a small and variable amount of SiOH groups may also be present; and by the company Shin-Etsu under the references KR-220L, which are composed of T units of formula CH3SiO3/2 and have Si—OH (silanol) end groups, under the reference KR-242A, which comprise 98% of T units and 2% of dimethyl D units and have Si—OH end groups or alternatively under the reference KR-251 comprising 88% of T units and 12% of dimethyl D units and have Si—OH end groups.

Examples of commercially available polypropylsilsesquioxane resins that may be mentioned include those sold: by the company Dow Corning under the reference Dow Corning 670 Fluid or 680 Fluid. Typically such commercially available products are polypropylsilsesquioxane diluted in volatile oil such as volatile hydrocarbon oil or volatile silicone oil such as D5. Dow Corning 670 and 680 Fluids have a general formula of RnSiO(4-n)/2 wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises RSiO3/2 units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5,000, 7,000, 10,000, 15,000, 20,000, 25,000 to about 30,000, 50,000, 75,000, 100,000 g/mol and a Tg of less than about 37° C., from about −100, −50, −37, or −20 to about 37° C.

Examples of commercially available polyphenylsilsesquioxane resins that may be mentioned include those sold: by the company Dow Corning under the reference Dow Corning 217 Flake Resin, which is a polyphenylsilsesquioxane with silanol end groups; and by the company Wacker under the reference Belsil SPR 45 VP.

Silicone Acrylate Copolymer

Suitable silicone acrylate copolymers include polymers comprising a siloxane group and a hydrocarbon group. In some embodiments, such silicone acrylate copolymers comprise at least about 10%, 20%, 30%, 40%, 50%, 60%, 70%, 80%, or 90% silicone by weight. For example, suitable polymers include polymers comprising a hydrocarbon backbone such as, for example, a backbone chosen from vinyl polymers, methacrylic polymers, and/or acrylic polymers and at least one chain chosen from pendant siloxane groups, and polymers comprising a backbone of siloxane groups and at least one pendant hydrocarbon chain such as, for example, a pendant vinyl, methacrylic and/or acrylic groups.

The at least one silicone acrylate copolymer can be chosen from silicone/(meth)acrylate copolymers, such as those as described in U.S. Pat. Nos. 5,061,481, 5,219,560, and 5,262,087, and U.S. patent application 2012/0301415, the entire contents of all of which are hereby incorporated by reference.

The at least one silicone acrylate copolymer may be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/ dimethicone copolymer), KP-550 (INCI name: isododecane (and) acrylate/dimethicone copolymer), KP-561 (acrylates/stearyl acrylate/dimethicone acrylates copolymer), KP-562 (acrylates/behenyl acrylate/dimethicone acrylates copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples of such polymers and their synthesis are disclosed, for example, in U.S. Pat. Nos. 4,972,037, 5,061,481, 5,209,924, 5,849,275, and 6,033,650, and PCT applications WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate copolymers include silicone/acrylate graft terpolymers, for example, the copolymers described in PCT application WO 01/32727, the disclosure of which is hereby incorporated by reference.

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Suitable silicone acrylate copolymers include silicone/(meth)acrylate copolymers, such as those as described in U.S. Pat. Nos. 5,061,481, 5,219,560, and 5,262,087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545.

Other non-limiting examples of silicone film formers suitable for use in the present invention are silicone esters comprising units of formulae (A) and (B), disclosed in U.S. Pat. Nos. 6,045,782, 5,334,737, and 4,725,658, the disclosures of which are hereby incorporated by reference:

$$R_a RE_b SiO_{[4-(a+b)/2]} \quad (A)$$

and $$R'_x RE_y SiO_{1/2} \quad (B)$$

Wherein R and R', which may be identical or different, are each chosen from optionally substituted hydrocarbon groups;

a and b, which may be identical or different, are each a number ranging from 0 to 3, with the proviso that the sum of a and b is a number ranging from 1 to 3;

x and y, which may be identical or different, are each a number ranging from 0 to 3, with the proviso that the sum of x and y is a number ranging from 1 to 3;

RE, which may be identical or different, are each chosen from groups comprising at least one carboxylic ester.

According to preferred embodiments, RE groups are chosen from groups comprising at least one ester group formed from the reaction of at least one acid and at least one alcohol. According to preferred embodiments, the at least one acid comprises at least two carbon atoms. According to preferred embodiments, the at least one alcohol comprises at least ten carbon atoms. Non-limiting examples of the at least one acid include branched acids such as isostearic acid, and linear acids such as behenic acid. Non-limiting examples of the at least one alcohol include monohydric alcohols and polyhydric alcohols, such as n-propanol and branched etheralkanols such as (3,3,3-trimethylolpropoxy)propane.

Further non-limiting examples of the at least one silicone acrylate copolymer film former include liquid siloxy silicates and silicone esters such as those disclosed in U.S. Pat. No. 5,334,737, the disclosure of which is hereby incorporated by reference, such as diisostearoyl trimethylolpropane siloxysilicate and dilauroyl trimethylolpropane siloxy silicate, which are commercially available from General Electric under the tradenames SF 1318 and SF 1312, respectively.

According to one or more embodiments of the present invention, Component A comprises at least one silicone acrylate and at least one silicone resin. Preferably, the at least one silicone resin is a polypropylsilsesquioxane resin.

According to preferred embodiments, the film forming agent(s) is/are preferably present in an amount of from about 0.01%, 0.05%, 0.080%, 10%, 20%, 30%, 40%, 80%, 80%, 70%, 80%, 90%, 10%, 11%, 12%, 13%, 14%, 15%, 20%, 25%, 30%, 35% to about 20%, 25%, 30%, 35%, 40%, 50%, 60%, 70%, 80% or 90%. In one or more embodiments, these amounts pertain to the amount of silicone-containing film forming agent. In some embodiments, these amounts pertain to the total amount of film forming agents if there are others present besides the at least one silicone-containing film forming agent. In further embodiments, the film forming agent(s) is/are preferably present in an amount of from about 0.01% to about 90% by weight, preferably from 0.08% to 80% by weight, and preferably from 0.1% to 60% by weight of the total weight of the component in which they are found, including all ranges and subranges therebetween.

Silicone Compounds

In one or more embodiments, Component B comprises one or more silicone compounds. As used herein, "silicone compound" refers to a compound comprising silicone having a surface energy lower than that of the silicone-containing film forming agents in Component A. In one or more embodiments, the term refers to a compound, which may be polymeric, comprising a silicon bonded to a minimum of one oxygen, and in even further embodiments, two oxygens. In some embodiments, the silicon is bonded to a hydrocarbon (e.g., C1-22 linear, branched, and/or aryl). In further embodiments, the hydrocarbon is selected from the group consisting of methyl, ethyl, propyl, and phenyl. In one or more embodiments, the silicone compound comprises a polydimethylsiloxane (PDMS). In some embodiments, the silicone compound itself may be linear, branched or dendritic. In further embodiments, the silicone compound is linear or substantially linear. In one or more embodiments, the silicone compound comprises a chain termination selected from the group consisting of hydrocarbon, alcohol, ester, acid, ketone, amine, amide, epoxy, vinylogous (e.g. alkene or alkyne group), halogen, hydride, and the like. For example, in embodiments where the silicone compound comprises polydimethylsiloxane, the compound may be chain end terminated with an —OH or a methyl group.

In one or more embodiments, the term "silicone compound" includes, but is not limited to, silicone gums, silicone fluids, silicone wax, and the like. The silicone compounds may impart properties on the composition (e.g., enhance shine or matte quality). In one or more embodiments, the silicone compounds are present in an amount sufficient to achieve a viscosity of greater than about 1,000 cSt and/or less than about 22,000,000 cSt. In some embodiments, the viscosity ranges from about 1,000, 5,000, 10,000, 20,000, 30,000, 40,000, 50,000 or 60,000 cSt to about 100,000, 200,000, 300,000, 400,000, 500,000, 600,000, 700,000, 800,000, 900,000, 1,000,000, 5,000,000, 10,000,000 or 22,000,000 cSt. In one or more embodiments, the silicone compounds are present in an amount sufficient to achieve a viscosity ranging from about 10,000, 15,000, 20,000, 25,000, 30,000, 35,000 or 40,000 to about 60,000, 65,000, 70,000, 80,000 90,000 or 100,000.

Comfort Agent

The cosmetic compositions described herein comprise at least one siloxane polymer wax. While not wishing to be bound to any particular theory, it is thought that the siloxane polymer wax provides additional comfort and/or slip feeling to the user. In some embodiments, the siloxane polymer wax is selected from the group consisting of bis-stearyl dimethicone, stearyl dimethicone, bis stearoxy dimethicone, and combinations thereof. The siloxane polymer wax may be present in an amount of from about 0.01, 0.05, 0.1, 0.5, 1, 1.5, 2, 2.5, 3, 3.5, 4, 4.5, 5, 5.5, 6, 6.5 or 7 to about 4, 4.5, 5, 5.6, 6, 6.5, 7, 7.5, 8, 8.5, 10, 11, 12, 13, 14, 15, 16, 17, 18, 19 or 20% by weight with respect to the total weight of the composition.

Shine/Luminosity Enhancing Agents

According to preferred embodiments of the present invention, at least one shine enhancing agent can be added to Component A, Component B, or both. Such shine enhancing agents may impart a luminous and/or dewy effect to compositions described herein, which may be advantageous in the case of foundation compositions or shine effect in the case of lip compositions. The compositions of the present invention comprise at least one phenylated silicone is selected from the group consisting of trimethylsiloxyphenyl dimethicone, diphenylsiloxy phenyl trimethicone; trimethyl pentaphenyl trisiloxane; trimethyl pentaphenyl trisiloxane, and combinations thereof. The phenylated silicone may be present in an amount of from about 0.01, 0.05, 0.1, 0.5, 1, 1.5, 2, 2.5, 3, 3.5, 4, 4.5, 5, 5.5, 6, 6.5 or 7 to about 4, 4.5, 5, 5.6, 6, 6.5, 7, 7.5, 8, 8.5, 10, 11, 12, 13, 14, 15, 16, 17, 18, 19 or 20% by weight with respect to the total weight of the composition.

Additional shine enhancing agents can be added. In some embodiments, the shine enhancing agent is selected from the group consisting of agents, which facilitate self-leveling of a layer, agents which have a high refractive index, or mixtures thereof.

Suitable shine enhancing agents include those compounds having a refractive index ranging from about 1.45 to about 1.60, and a weight average molecular weight of less than 15,000, preferably less than 10,000, and preferably less than 2,000. Examples of such agents include, but are not limited to, phenylated silicones such as those commercialized under the trade name "ABIL AV 8853" by Goldschmidt, those commercialized under the trade names "DC 554", "DC 555", "DC 556" and "SF 558" by Dow Corning, and those commercialized under the trade name "SILBIONE 70633 V 30" by Rhone-Poulenc.

Additional examples of suitable phenylated silicones include, but are not limited to, those commercialized by Wacker Silicones such as BELSIL PDM 20, a phenylated silicone with a viscosity at 25° C. of approximately 20 cSt; BELSIL PDM 200, a phenylated silicone with a viscosity at 25° C. of approximately 200 cSt; BELSIL PDM 1000, a phenylated silicone with a viscosity at 25° C. of approximately 1000 cSt.

Additional examples of suitable shine enhancing agents include, but are not limited to, polycyclopentadiene, poly (propylene glycol) dibenzoate (nD=1.5345), aminopropyl phenyl trimethicone (nD=1.49-1.51), pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

Particularly preferred shine enhancing agents are the phenylated silicones such as phenyl trimethicone, and trimethyl pentaphenyl trisiloxane, and esters such as pentaerythrityl tetraoleate, and PPG-3 benzyl ether myristate.

Suitable shine enhancing agents include those which provide self-leveling properties to the compositions of the present invention. Suitable examples of such compositions include, but are not limited to, the silicone gums discussed below.

The silicone gum can correspond to the formula:

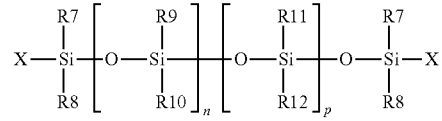

in which:
R7, R8, R11 and R12 are identical or different, and each is chosen from alkyl radicals comprising from 1 to 6 carbon atoms,
R9 and R10 are identical or different, and each is chosen from alkyl radicals comprising from 1 to 6 carbon atoms and aryl radicals,
X is chosen from alkyl radicals comprising from 1 to 6 carbon atoms, a hydroxyl radical and a vinyl radical,
n and p are chosen so as to give the silicone gum a viscosity of from 350 cSt to 50,000,000 cSt, preferably from 500 cSt to 40,000,000 cSt, preferably from 750 cSt to 30,000,000 cSt, preferably from 850 cSt to 20,000,000 cSt, preferably from 950 cSt to 18,000,000 cSt and preferably from 1000 cSt to 10,000,000 cSt, including all ranges and subranges therebetween. A particularly preferred range is from 20,000 cSt to 800,000 cSt, with 25,000 cSt to 750,000 cSt being most preferred.

In general, n and p can each take values ranging from 0 to 10,000, such as from 0 to 5,000.

Among the silicone gums which can be used according to the invention, mention may be made of those for which:
the substituents R7 to R12 and X represent a methyl group, p=0 and n=2 700, such as the product sold or made under the name SE30 by the company General Electric,
the substituents R7 to R12 and X represent a methyl group, p=0 and n=2 300, such as the product sold or made under the name AK 500 000 by the company Wacker,
the substituents R7 to R12 represent a methyl group, the substituent X represents a hydroxyl group, p=0 and n=2 700, as a 13% solution in cyclopentasiloxane, such as the product sold or made under the name Q2-1401 by the company Dow Corning, the substituents R7 to R12 represent a methyl group, the substituent X represents a hydroxyl group, p=0 and n=2 700, as a 13% solution in polydimethylsiloxane, such as the product sold or made under the name Q2-1403 by the company Dow Corning, and the substituents R7, R8, R11, R12 and X represent a methyl group and the substituents R9 and R10 represent an aryl group, such that the molecular weight of the gum is about 600 000, for instance the product sold or made under the name 761 by the company Rhone-Poulenc (Rhodia Chimie).

In preferred embodiments, the silicone gum correspond to the following formula:

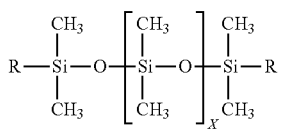

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cycohexyl, phenyl, and mixtures thereof. The silicone gums employed in the present invention may be terminated by triorganosilyl groups of the formula R'3 where R' is a radical of monovalent hydrocarbons containing from 1 to 6 carbon atoms, hydroxyl groups, alkoxyl groups and mixtures thereof.

According to preferred embodiments, Component B/Layer B comprises at least one shine (gloss) enhancing agent.

According to preferred embodiments, Component B/Layer B has a self-leveling property which results in a flatter interface between Layer A and Layer B and/or between Layer B and air, and this flatter interface results in light diffraction, refraction and/or reflection properties for Layer B which enhances the shine of the composition.

According to preferred embodiments of the present invention, at least two silicone compounds such as silicone fluids (for example, phenylated silicones described above) and/or silicone gums are present in the compositions of the present invention.

According to preferred embodiments, if present, agent(s) which facilitate self-leveling of a layer such as silicone gum(s) is/are preferably present in an amount of from about 0.01% to about 90% by weight, preferably from 1% to 85% by weight, and preferably from 5% to 80% by weight of the total weight of the composition, including all ranges and subranges therebetween.

According to preferred embodiments, if present, agent(s) which have a high refractive index such as phenylated silicone oil(s) is/are preferably present in an amount of from about 0.05% to about 90% by weight, preferably from 0.1% to 75% by weight, and preferably from 1% to 50% by weight of the total weight of the composition, including all ranges and subranges therbetween.

According to preferred embodiments of the present invention, at least two silicone compounds such as silicone fluids (for example, phenylated silicones described above) and/or silicone gums are present in the compositions of the present invention.

According to preferred embodiments, the shine enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Matte Enhancing Agents (Mattifying Agent)

According to preferred embodiments of the present invention, at least one matte enhancing agent can be added to Component A, Component B, or both. With respect to Component B, the at least one matte enhancing agent can be added regardless of whether Component B is not self-leveling and/or Layer B has refractive properties to impart matte properties to the composition as described above.

Suitable matte enhancing agents include, but are not limited to, mattifying fillers such as, for example, talc, silica, silicone elastomers, and polyamides, and waxes such as, for example, beeswax and copernicia cerifera (carnauba) wax.

According to preferred embodiments, the matte enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Soft Focus Agents

According to one or more embodiments, the compositions described herein comprise a soft focus agent. As used herein, the term "soft focus" means that the visual appearance of the skin is more homogenous and matte, leading to the blurring or hiding of skin imperfections.

In some embodiments, the at least soft focus agent may be chosen from hydrophobic silica aerogel particles. Silica aerogels are porous materials obtained by replacing (by drying) the liquid component of a silica gel with air.

Hydrophobic silica aerogel particles useful according to embodiments of the disclosure include silylated silica (INCI name: silica silylate) aerogel particles. The preparation of hydrophobic silica aerogel particles that have been surface-modified by silylation is described more fully in U.S. Pat. No. 7,470,725, incorporated by reference herein. In various embodiments, aerogel particles of hydrophobic silica surface-modified with trimethylsilyl groups may be chosen. For example, the aerogel sold under the name VM-2260® by the company Dow Corning, the particles of which have an average size of about 1000 microns and a specific surface area per unit of mass ranging from 600 to 800 m2/g, or the aerogel sold under the name VM-2270®, also by the company Dow Corning, the particles of which have an average size ranging from 5 to 15 microns and a specific surface area per unit of mass ranging from 600 to 800 m2/g, may be chosen. In other embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1 100®, and Enova Aerogel MT 1200®, may be chosen.

Other soft-focus effect agents can be found in WO/2016100690, the entire contents of which are herein incorporated by reference.

Thickeners

According to preferred embodiments of the present invention, compositions comprise a thickener. The thickener may comprise a triester of glycerin and a fatty acid. In further embodiments, the triester of glycerin and a fatty acid comprises trihydroxystearin. The trimester of glycerin may be present from about 0.01, 0.05, 0.1, 0.5, 1, 1.5, 2, 2.5, 3, 3.5 or 4 to about 1, 1.5, 2, 2.5, 3, 3.5, 4, 5, 6, 7, 8, 9 or 10.

Coloring Agents

According to preferred embodiments of the present invention, compositions further comprising at least one coloring agent are provided. Preferably, such colored compositions can be cosmetic compositions such as, for example, lip compositions (for example, lipstick) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.01% to 40%, and further such as from 0.1% to 30%, including all ranges and subranges therebetween. In the case of certain products, the pigments, including nacreous pigments, may, for example, represent up to 50% by weight of the composition.

According to one or more embodiments of the present invention, the compositions comprise at least one pigment or filler, wherein the pigment or filler is surface surface-treated with a trialkoxyalkylsilane. The at least one pigment or filler surface-treated with a trialkoxyalkylsilane may be found in Component A (i.e., along with the hydrocarbon- and/or silicone-containing film forming agent).

Suppliers for the surface-treated pigments are available from Kobo, Daito Kasei, Gelest, Sensient, and Miyoshi.

In one or more embodiments, the pigment comprises a metal oxide (which is surface-treated with a trialkoxyalkylsilane). In further embodiments, the metal oxide comprises iron oxide, titatnium dioxide, zinc oxide, chromium oxide or combinations thereof. Fillers suitable to be surface-treated with trialkoxyalkylsilane include, but are not limited to, talc and mica. In some embodiments, the trialkoxysilane comprises triethoxycaprylylsilane.

The at least one pigment or filler surface-treated with a trialkoxyalkylsilane may be present in the composition in a concentration ranging up to 50% by weight of the total weight of the composition, such as from about 0.01, 0.05, 0.1, 0.5, 1, 2, 3, 4, 5, 6, 7, 8, 9, 10, 12, 15, 20% to 5, 6, 7, 8, 9, 10, 15, 20, 25, 30, 35 or 40%. In embodiments where there is more than one pigment present in the composition, the above amounts refer to the total amount of pigment.

In one or more embodiments, the composition further comprises more than one pigment. The additional pigments may be treated or untreated, provided that they remain stable in the composition. In some embodiments, the composition comprises a treated and an untreated organic pigment.

Oil Phase

According to preferred embodiments of the present invention, compositions further comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |

TABLE 1-continued

| Compound | Flash Point (° C.) | Viscosity (cSt) |
|---|---|---|
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:
 hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;
 synthetic oils or esters of formula R5COOR6 in which R5 represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with R6+R7≥10, such as, for example, Purcellin oil (cetostearyl octanoate), isononyl isononanoate, octyldodecyl neopentanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;
 synthetic ethers containing from 10 to 40 carbon atoms;
 C8 to C26 fatty alcohols, for instance oleyl alcohol, cetyl alcohol, stearyl alcohol, and cetearly alcohol; and
 mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments, if present, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to preferred embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula (R2R'SiO1/2)x(R"SiO3/2)y, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to preferred embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

If present, the wax or waxes may be present in an amount ranging from 1 to 30% by weight relative to the total weight of the composition, for example from 2 to 20%, and for example from 3 to 10%, including all ranges and subranges therebetween.

Methods

According to preferred embodiments of the present invention, methods of treating, caring for and/or making up keratinous material, such as skin, by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

According to preferred embodiments of the present invention, methods of applying compositions of the present invention to a keratinous material (for example, skin and/or lips) comprising mixing or blending the composition so that the immiscible components are temporarily miscible, and applying the composition comprising the temporarily miscible components to the keratinous material are provided. In one or more embodiments, composition may be mixed in a mixing pack or may be mixed by hand. Subsequent to application to the keratinous material, the components separate to form a multilayer structure on the keratinous material.

According to preferred embodiments of the present invention, kits comprising (1) at least one container; (2) at least one applicator; and (3) at least one cosmetic composition capable of forming a multilayer structure after application to a keratinous material, wherein the composition comprises at least two immiscible components prior to application.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Also in accordance with the preceding preferred embodiments, compositions are preferably contained in a suitable container for cosmetic compositions. Suitable shapes of such containers include, but are not limited to, any geometric shape such as, for example, square, rectangular, pyramidal, oval, circular, hemispherical, etc. Further, the container may be made of flexible or inflexible material.

Similarly, any applicator suitable for application of cosmetic compositions can be used in accordance with the present invention, with suitable examples of types of applicators including, but not limited to, a brush, stick, pad, roller ball, etc.

Preferably, either (1) the container is capable of mixing or blending the composition of the present invention so that the immiscible components are temporarily miscible; (2) the applicator is capable of mixing or blending the composition of the present invention so that the immiscible components are temporarily miscible; or (3) the container and the applicator working together are capable of mixing or blending the composition of the present invention so that the immiscible components are temporarily miscible in accordance with the preceding preferred embodiments. For example, a flexible container by virtue of its flexibility could create sufficient forces when manipulated to temporarily mix or blend the composition of the present invention so that the immiscible components are temporarily miscible; an applicator by virtue of its design could create sufficient forces when withdrawn from the container to temporarily mix or blend the composition of the present invention so that the immiscible components are temporarily miscible; or (3) an inflexible container and an applicator by virtue of their synergistic design elements could create sufficient forces when the applicator is withdrawn from the container to temporarily mix or blend the composition of the present invention so that the immiscible components are temporarily miscible.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Preparation

Several liquid lipstick formulas were prepared containing the ingredients shown below in Table 3. The mixture of pigment and film formers was processed to create a pigment dispersion. The blend was processed using a Disconti Mill until the dispersion passed the Hegman Gauge test (ASTM D1210-05). Dimethiconol and dimethicones were mixed with high shear until homogeneous. Then, the pigment dispersion, silicone mixture and the remaining ingredients were combined stirring at 60° C. until homogeneous liquid composition was obtained. After that, the samples were cooled down to the room temperature and transferred to desired containers and/or applicators.

TABLE 3

| | Inventive Formulas | | | | |
|---|---|---|---|---|---|
| | INCI US | Ex. 1 | Ex. 2 | Ex. 3 | Ex. 4 |
| PHENYLATED SILICONE | TRIMETHYLSILOXYPHENYL DIMETHICONE | 4 | 0 | 9 | 3 |
| FILM FORMER | POLYPROPYL-SILSESQUIOXANE | 22.32 | 22.32 | 22.32 | 22.32 |
| FILM FORMER | ACRYLATES/DIMETHICONE COPOLYMER | 10.40 | 10.40 | 10.40 | 10.40 |
| SILOXANE POLYMER WAX | BIS-STEARYL DIMETHICONE | 8 | 12 | 4.8 | 10 |
| TRIESTER OF GLYCERIN AND FATTY ACID | TRIHYDROXYSTEARIN | 0 | 0 | 0.5 | 0.5 |
| SOLVENT | ISODODECANE | 28.78 | 28.78 | 26.48 | 27.28 |
| PIGMENT | PIGMENT | 6 | 6 | 6 | 6 |
| SILICONE COMPOUND | DIMETHICONE/DIMETHICONOL BLEND (40,000-65,000 cSt) | 20.5 | 20.5 | 20.5 | 20.5 |

Inventive Examples 1-4 were compared to Comparative Examples 5-6. Comparative Example 5 had the ingredients shown below in Table 5.

TABLE 4

| | Comparative Formula | |
|---|---|---|
| | INCI US | Comp. Ex. 5 |
| FILM FORMER | POLYPROPYL-SILSESQUIOXANE | 22.32 |
| FILM FORMER | ACRYLATES/DIMETHICONE COPOLYMER | 10.4 |
| SOLVENT | ISODODECANE | 40.778 |
| PIGMENT | PIGMENT | 6.002 |
| SILICONE COMPOUND | DIMETHICONE/DIMETHICONOL BLEND (40,000-65,000 cSt) | 20.5 |

In Vitro Shine Measurement

Films of each formula were deposited onto contrast cards using a 3 MIL drawdown bar and an Automatic Drawdown Machine. The films were dried at 40° C. overnight, then analyzed using a gloss meter (BYK: micro-TRI-gloss) at an angle of 20° and 60°. The results are shown below in Table 5.

TABLE 5

| | In Vitro Shine Results | | | | |
|---|---|---|---|---|---|
| | Ex. 1 | Ex. 2 | Ex. 3 | Ex. 4 | Comp. Ex. 5 |
| Shine 20° | 60.3 ± 2.3 | 56.3 ± 5.9 | 51.8 ± 1.4 | 56.3 ± 7.8 | 39.2 ± 2.1 |
| Shine 60° | 70.4 ± 0.2 | 70.4 ± 0.3 | 68.4 ± 5.7 | 70.2 ± 7.4 | 66.3 ± 1.1 |

As can be seen from the above, the inventive examples demonstrated more shine than the comparative, particularly at an angle 20°.

What is claimed is:

1. A cosmetic composition that forms a multilayer structure after application to a keratinous material, the cosmetic composition comprising:
   (a) Component A which comprises:
      (i) about 0.01% to 60% by weight with respect to the total weight of the composition of at least one silicone-containing film forming agent having at least one glass transition temperature which is lower than normal human body temperature, wherein the at least one silicone-containing film forming agent is selected from the group consisting of a silicone resin, a silicone acrylate copolymer, and mixtures thereof;
      (ii) about 0.01 to 20% by weight with respect to the total weight of the composition of at least one phenylated silicone;
      (iii) about 0.01 to 20% by weight with respect to the total weight of the composition of at least one siloxane polymer wax; and
   (b) Component B which comprises:
      (i) about 0.01% to 90% by weight with respect to the total weight of the composition of at least one silicone compound sufficient to achieve a viscosity of about 1,000 cSt to 10,000,000 cSt;
      wherein the Component A and Component B are immiscible, the Component B has a surface energy that is lower than that of Component A, and the at least one silicone compound of Component B have a surface energy that is lower than that of the at least one silicone-containing film forming agent of Component A,
      wherein the weight ratio of silicone-containing film forming agent(s) in Component A to silicone compound(s) in Component B is from about 1:50 to 50:1, and
      wherein the cosmetic composition forms a multi-layer structure after application to a keratinous material.

2. The cosmetic composition of claim 1, wherein the cosmetic composition comprises at least two immiscible components prior to application.

3. The cosmetic composition of claim 1, wherein the cosmetic composition is anhydrous.

4. The cosmetic composition of claim 1, wherein the at least one phenylated silicone is selected from the group consisting of trimethylsiloxyphenyl dimethicone, diphenylsiloxy phenyl trimethicone; trimethyl pentaphenyl trisiloxane; trimethyl pentaphenyl trisiloxane, and combinations thereof.

5. The cosmetic composition of claim 1, wherein the at least one siloxane polymer wax is selected from the group consisting of bis-stearyl dimethicone, stearyl dimethicone, bis stearoxy dimethicone, and combinations thereof.

6. The cosmetic composition of claim 1, further comprising:
   (iv) about 0.01 to 10% by weight with respect to the total weight of the composition of at least one triester of glycerin and a fatty acid.

7. The cosmetic composition of claim 1, wherein the at least one silicone-containing and/or hydrocarbon-containing film forming agent is present in an amount of about 15% to 60% by weight with respect to the total weight of the composition.

8. The cosmetic composition of claim 1, wherein the at least one silicone compound is present in amount of about 0.01% to about 80% by weight with respect to the total weight of the composition and in amounts sufficient to achieve a viscosity of 30,000 cSt to 70,000 cSt.

9. The cosmetic composition of claim 1, wherein the weight ratio of film forming agent(s) in Component A to silicone compound(s) in Component B is from 50:1 to 1:2.

10. The cosmetic composition of claim 1, wherein the at least one silicone-containing film forming agent comprises a silsesquioxane.

11. The cosmetic composition of claim 1, wherein cosmetic composition does not comprise a fluorinated compound.

12. A kit comprising:
   (a) the cosmetic composition according to claim 1;
   (b) at least one container which contains the cosmetic composition according to claim 1; and
   (c) at least one applicator.

13. A method of applying the cosmetic composition of claim 1 to a keratinous material comprising mixing the cosmetic composition to form a mixed composition in which Component A and Component B are temporarily miscible, and applying the mixed composition to the keratinous material.

14. A cosmetic composition capable of forming that forms a multilayer structure after application to a keratinous material, the cosmetic composition comprising:
   (a) Component A which comprises:
      (i) about 20% to 40% by weight with respect to the total weight of the composition of at least one silicone-containing film forming agent selected from the group consisting of polypropylsilsesquioxane, acrylates/dimethicone copolymer and combinations thereof;
      (ii) about 5 to 15% by weight with respect to the total weight of the composition of at least one phenylated silicone;
      (iii) about 1 to 15% by weight with respect to the total weight of the composition of at least one siloxane polymer wax;
      (iv) about 0.1 to 2% by weight with respect to the total weight of the composition of at least one triester of glycerin and a fatty acid; and
   (b) Component B which comprises:
      (i) about 10% to 30% by weight with respect to the total weight of the composition of at least one silicone compound selected from the group consisting of dimethicone, dimethiconol and combinations thereof sufficient to achieve a viscosity of about 1,000 cSt to 100,000 cSt;
      wherein the Component A and Component B are immiscible at temperatures below 50° C., the Component B has a surface energy that is lower than that of Component A, and the at least one silicone compound of Component B has a surface energy that is lower than that of the at least one silicone-containing film forming agent of Component A,
      wherein the weight ratio of the at least one silicone-containing film forming agent in Component A to the at least one silicone compound in Component B is from about 50:1 to 1:2, and
      wherein the cosmetic composition forms a multilayer structure after application to a keratinous material.

15. The cosmetic composition of claim 1, wherein the cosmetic composition forms a multilayer structure comprising a first layer formed predominately of Component A and a second layer formed predominately of Component B.

16. The cosmetic composition of claim 1, wherein the cosmetic composition forms a multilayer structure comprising a first layer and a second layer, the first layer being disposed between the keratinous material and the second layer.

17. The cosmetic composition of claim 14, wherein the surface energy of Component A is closer to the surface energy of the keratinous material than the surface energy of Component B.

18. The cosmetic composition of claim 14, wherein the surface energy of Component A is about 36 mN/m.

19. The cosmetic composition of claim 1, wherein Component A and Component B have a density difference of 0.001-1 kg/m$^3$.

20. The cosmetic composition of claim 1, wherein Component A and Component B are immiscible at temperatures below 50° C.

* * * * *